(12) United States Patent
Muir et al.

(10) Patent No.: US 6,355,249 B2
(45) Date of Patent: *Mar. 12, 2002

(54) **PROCESS FOR RECOVERY AND PURIFICATION OF SAPONINS AND SAPOGENINS FROM QUINOA (*CHENOPODIUM QUINOA*)**

(75) Inventors: Alister D. Muir; David Paton; Krista Ballantyne; Andrew A. Aubin, all of Saskatoon (CA)

(73) Assignee: Her Majesty the Queen in right of Canada, as represented by the Minister of Agriculture and Agri-Food Canada, Saskatoon (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,159

(22) Filed: Apr. 16, 1999

Related U.S. Application Data

(60) Provisional application No. 60/082,262, filed on Apr. 17, 1998.

(51) Int. Cl.[7] .......................... A61K 35/78; A61K 31/70
(52) U.S. Cl. ....................... 424/195.1; 514/25; 514/783
(58) Field of Search .................... 424/195.1; 514/25, 514/783

(56) References Cited

U.S. PATENT DOCUMENTS

| 2,791,581 A | 5/1957 | Wall et al. ............... 260/210.5 |
| 2,960,500 A | 11/1960 | Holt et al. ............. 260/239.55 |
| 3,019,220 A | 1/1962 | Julian ..................... 260/239.55 |
| 3,351,582 A | 11/1967 | Balansard et al. ....... 260/210.5 |
| 3,883,425 A | 5/1975 | Dorn ........................... 210/23 |
| 4,004,976 A | 1/1977 | Isaac ............................. 195/2 |
| 4,033,818 A | 7/1977 | Pourrat et al. ................. 195/7 |

(List continued on next page.)

FOREIGN PATENT DOCUMENTS

| CA | 2167075 | 7/1994 |
| WO | WO 96/38161 | 12/1996 |

OTHER PUBLICATIONS

Honerlagen V. H. and Tretter N., "Zur routinemäβigen quantitativen Gesamtsaponinbestimmung in Radix Ginseng Panax und Extrakten", Deutsche Apotheker Zeitung, 119 (38), 1483–1486, 1979, cited on p. 129, lower part of D1.

Mizui et al., "Sapponins from Brans of Quinoa, *Chenopodium quinoa* Willd. I", Chem. Pharm. Bull., vol. 36(4): 1415–1418, 1988.*

(List continued on next page.)

*Primary Examiner*—Gary Geist
*Assistant Examiner*—Devesh Khare

(57) ABSTRACT

A process for commercial extraction of saponins from quinoa, and optionally for the formation of corresponding sapogenins. The saponin extraction process comprises contacting a saponin-containing part of a quinoa plant with an aqueous alcohol solution containing an alcohol selected from the group consisting of methanol and ethanol to form a saponin-containing solution and an extracted solid residue, removing the alcohol from the saponin-containing solution to leave a saponin-containing aqueous solution, and evaporating water from the saponin-containing aqueous solution to produce a saponin-containing product. The conversion to sapogenins involves obtaining a solution of saponins in an aqueous alcohol, adding a strong acid to the solution to hydrolyze the saponins to form corresponding sapogenins that precipitates out of the solution as a precipitate, recovering the precipitate, and decolorizing the precipitate by forming a slurry of the precipitate with a solution of an aqueous base to form a decolorized sapogenin product.

50 Claims, 9 Drawing Sheets

U.S. PATENT DOCUMENTS

| | | | |
|---|---|---|---|
| 4,335,113 A | 6/1982 | Combier et al. | 424/180 |
| 4,350,688 A | 9/1982 | Schmittmann | 424/182 |
| 4,501,734 A | 2/1985 | Tanaka et al. | 514/198 |
| 4,524,067 A | 6/1985 | Arichi et al. | 514/33 |
| 4,808,629 A | 2/1989 | Liu | 514/557 |
| 4,985,248 A | 1/1991 | Liu | 424/195.1 |
| 5,057,540 A | 10/1991 | Kensil et al. | 514/25 |
| 5,086,043 A | 2/1992 | Liu | 514/25 |
| 5,098,710 A | 3/1992 | Liu | 424/195.1 |
| 5,443,829 A | 8/1995 | Kensil et al. | 424/195.1 |
| 5,597,807 A | 1/1997 | Estrada et al. | 514/26 |
| 5,688,772 A | 11/1997 | Estrada et al. | 514/25 |

OTHER PUBLICATIONS

Gee et al., "Saponins of Quinoa (*Chenopodia quinoa*): Effects of Processing on their Abundance in Quinoa Products and their Biological Effects on Intestinal Mucosal Tissue", J. Sci. Food. Agric., vol. 63: 201–209, 1993.*

Jacobsen, S.E., "Developmental stability of *quinoa* under European conditions", Industrial Crops and Products, vol. 7: 169–174, 1998.*

Ruiz et al., "Determinacion de acido oleanolico, por cromatografia gas liquida, en quinua", Bol. Soc. Quim. Peru, vol. 45(3): 266–276, 1979 (Application Provided Translation w/Suppl. IDS of Feb. 14, 2000).*

Ruiz et al., Evaluacion de cuatro metodos gas chromatogrficos para determinar acido oleanolico en quinua (*Chenopodium quinoa*, Willd, Var. Kcancolla), Bol. Soc. Quim. Peru, vol. 46(1):76–84, 1980.*

Meyer et al., Bioactivity–Directed Isolation and Characterization of Quinoside A: One of the Toxic/Bitter Principles of Quinoa Seeds (*Chenopodium quinoa* Willd.), J. Agric. Food Chem., vol. 38: 205–208, 1990.*

Ma et al., "Additional Toxic, Bitter Saponins From the Seeds of *Chenopodium quinoa*", J. Natl. Prod., vol. 52(5): 1132–1135, 1989.*

Penafiel et al., Determination Espectrfotometrica de Acido Olenolicoy Saponinas de quinua (*Chenopodium wuinoa* Willd, variedad Kancolla), Arch. Latinoam. Nutr., vol. 38(1): 113–131, 1988 (Applicant Provided Translation w/Suppl. IDS of Feb. 14, 2000).*

Amaya–Farfan, J. et al., *Fifth International Congress of Food Science & Technology—Food Availability and Quality through Technology and Science—Abstracts*, "Removal of Saponins from Quinua (*Chenopodium quinoa* Wild), Grain by Milling," *2b–13, p. 101, Kyoto, Japan Sep. 17–22, 1978.

M. Rajasekaran et al., *Journal of Ethnopharmacology*, "Antifertility Effect in Male Rats of Oleanolic Acid, a Triterpene from Eugenai Jambolana Flowers," pp. 115–121, vol. 24(1988), Elservier Scientific Publishers Ireland Ltd.

Fumie Mizui et al., *Chem. Pharm. Bull.*, "Saponins from Bran of Quinoa, *Chenopodium quinoa* Willd. II," pp. 375–377, vol. 38, No. 2, Feb. 1990.

Kaoru Umehara et al., *Chem. Pharm. Bull.*, "Studies on Differntiation–Inducing Activities of Triterpenes," pp. 401–405, vol. 40, No. 2, Feb. 1993.

Hisashi Matsuda et al., *Biol. Pharm. Bull.*, "Inhibitory Mechanisms of Oleanolic Acid 3–O–Monodesmosides on Glucose Absorption in Rats," pp. 717–719, vol. 20, No. 6. Jun. 1997.

Chemical and Biological Evalution of Quinoa (*Chenopodium quinoa* Willd). Effect of the Extraction of Saponins by Thermal Treatment by Mario L. Telleria Rios, Valdemiro C. Sgarbieri and Jaime Amaya–F.

* cited by examiner

PROCESS FOR RECOVERY AND PURIFICATION OF SAPONINS AND SAPOGENINS FROM QUINOA (CHENOPODIUM QUINOA)

CROSS-REFERENCE TO RELATED APPLICATION

This application claims the priority right of prior provisional patent application Ser. No. 60/082,262 filed Apr. 17, 1998 (pending) by applicants herein.

BACKGROUND OF THE INVENTION

1. Field of the Invention

The present invention relates generally to the cost-effective recovery of saponins and sapogenins from plant material. In particular, the invention relates to the recovery of saponins and sapogenins from Chenopodium quinoa (Quinoa) (Chenopodiaceae) grain, bran and other plant parts in substantially pure and commercially useful forms.

2. Description of Related Art

The high levels of saponins found in certain plants has long been thought to be responsible for the medicinal effects of some of these plants (Waller, G. R. and K. Yamasaki, Saponins used in Traditional and Modern Medicine, Advances in Experimental Medicine and Biology, Vol.404, 1996, New York: Plenum Press). The presence of high levels of saponins in the seeds of plants such as Quinoa (Chenopodium quinoa) has restricted the use of the human consumption of this grain.

Quinoa originates from the Andes region of South America where it was a staple grain in pre-Spanish Conquest times. Traditional use declined after the Spanish Conquest (Galwey, N. W., et al., Food Sci. Nutr., 42F:245, 1990) and cultivation and use of the grain was not widespread until a recent revival due to western interest in this crop as a high lysine, high protein grain for human consumption (De Bruin, A., J. Food Sci., 26:872,1964). The principal obstacle to wider human consumption of this grain has and continues to be the bitter taste of the saponin content of the grain. These saponins have been shown to be anti-nutritive in animal studies (Gee, J. M., et al.,J. Sci. FoodAgric., 63:201, 1993). In traditional use, the saponin content of the grain was reduced to acceptable levels by washing the grain in running water.

Since the revival of interest in Quinoa, a number of attempts have been made to devise practical methods to reduce the saponin content (Amaya-Farfan, J., et al., Removal of saponins from quinoa (Chenopodium quinoa Willd) grain by milling, 5th Int. Congr. Food Sci. Technol., Kyoto, Japan (1978); Gee, J. M., et al.,J. Sci. FoodAgric., 63:201,1993; Reichert, R. D., et al., Cereal Chem. 63:471, 1986; Galwey, N. W., et al., Food Sci. Nutr. 42F:245, 1990; Rios, M. L. T., et al., Arch Latinoamer Nutr. 28:253, 1978; Ridout, C. L., et al., J. Sci. Food Agric. 54:165, 1991), including combinations of milling and washing. In all cases the saponin rich fraction was considered to be a waste product and was discarded.

The recent interest in nutraceuticals and the medicinal properties of plants has resulted in studies that have attributed the biological activity of many of these plants to their saponin content. Many interesting physiological and pharmacological effects have been attributed to saponins and/or the corresponding sapogenins including reduction of serum cholesterol (Price et al., CRC Crit. Rev. Food Sci. Nutr. 26:27 (1987)), inhibition of alcohol absorption (Yoshikawa, M. & J. Yamahara (1996), In Saponins used in Traditional and Modern Medicine, Edited by G. R. Waller and K. Yamasaki. pp.207–218. New York, Plenum Press, Vol. 404), inhibition of glucose absorption (Matsuda, H., et al., Biol. Pharmac. Bull. 20:717, 1997), facilitation of transdermal absorption and intestinal absorption of drugs (Gee, et al. Toxic. in Vitro 3:85 (1989)), hypoglycaemic and anti-inflammatory effects (Honda, T., et al., Bioorganic Med. Chem. Lett. 7:1623,1997). Recently studies have shown that novel derivatives of the sapogenin oleanolic acid have potentially valuable pharmacological properties (Finlay, H. J., et al., Bioorganic Med. Chem. Lett. 7:1769,1997).

Saponins have been known to have adjuvant activity since the 1920's (Sjölander & Cox, Adv. Drug Delivery Rev. 34:321 (1998)), and a significant body of research has been conducted to explore these properties, particularly with saponin containing extracts of Quillaia saponaria. Kensil (Kensil, et al., J. Immunol. 146:431(1991)) has demonstrated that a need exists for a substantially pure saponin that can be used as an adjuvant in relatively low quantities with low toxicity and side effects. Estrada et al. U.S. Pat. No. 5,688,772 teaches that all quinoa saponins obtained by water extraction are equivalent and active as immunological adjuvants.

In spite of this interest, only a very limited number of purified saponins and sapogenins are commercially available and practical procedures for large scale quantitative and qualitative recovery of highly purified saponins and sapogenins are lacking in spite of numerous publications describing analytical and laboratory scale procedures. The lack of suitable practical extraction and purification methods is also reflected in the relatively high cost of those compounds that are available.

Traditionally, the saponin content in plant extracts has been determined by bioassay or by GLC analysis of the sapogenins derived by hydrolysis of the saponins (Ridout et al., J. Sci. Food Agric. 54:165 (1991)). GLC analysis in particular requires extensive clean up and hydrolysis prior to derivatization and analysis and this is reflected in the prior art for the extraction and purification of these compounds. Recent developments in HPLC analysis in our laboratories have indicated that, in the case of quinoa saponins, the GLC approach of extensive purification does not give quantitative or qualitative recovery of the naturally occurring saponins.

The chemical nature of the saponins found in quinoa has been the subject of several investigations (Mizui, F., et al. Chem. Pharm. Bull., 38:375 (1990)); however, the procedures used in these investigations for the recovery of the saponins is not practical and applicable for commercial scale production. The studies of Mizui et al. (Mizui, F., et al. Chem. Pharm. Bull., 38:375 (1990)) and others have shown that the saponins found in quinoa are of the triterpene type.

The prior art for isolation of saponins from quinoa falls into two categories: a) an aqueous extraction route typically as described in Estrada et al., 1997, U.S. Pat. Nos. 5,597,807 and 5,688,772; and b) a more traditional hot alcohol solvent (Mizui, F., et al. Chem. Pharm. Bull., 36:1415 (1988); Mizui, F., et al. Chem. Pharm. Bull., 38:375 (1990)). Surprisingly, the inventors of the present invention, have determined that neither the aqueous extraction route nor the hot alcohol extraction route are particularly efficient in recovery of quinoa saponins from bran, nor do either solvent extract the saponins from quinoa seed or bran on a qualitative basis. Estrada et al. U.S. Pat. No. 5,688,772 teaches that water extracts of quinoa (10 g of hulls extracted by 2×100 mL of water) contain all or most of the saponins present in quinoa.

Surprisingly, while the aqueous extraction method provides an extract with similar saponin profiles to that now known to be present in quinoa grain or bran, the yield was only 20% of that obtained by the process of the present invention. Mizui et al. [Mizui, F., et al. *Chem. Pharm. Bull.*, 36:1415(1988); Mizui, F., et al. *Chem. Pharm. Bull.*, 38:375 (1990)] demonstrated that saponins could be extracted from quinoa bran with hot methanol with yields of between 20 and 25% depending upon whether a subsequent hot 50% methanol extract was employed. These yields are significantly less than those achieved using the process of the present invention.

Surprisingly, the inventors have also shown that extraction with pure alcohols is highly selective in that methanol preferentially extracts only one of the three main saponins.

Surprising also is the very low yield of saponins obtained by this approach which is reflected not only in the results achieved by the present invention, but also in the very low yield of saponins obtained by Mizui et al. (1.66%).

The prior art for the purification of quinoa saponins is lacking in any specific details that would allow commercial scale production of these compounds. For example, Estrada et al., 1997 U.S. Pat. Nos. 5,597,807 and 5,688,772, and Estrada et al. Conun. *Immun. Microbial & Infect. Dis.* 21:225 (1998), teaches that quinoa saponins can be purified by dialysis against water or phosphate buffered saline (PBS) pH 7.2; however, since the inventors of the present invention have subsequently demonstrated that the aqueous extraction approach is not particularly efficient (10% of the weight of bran recovered as a saponin extract), and not the preferred extraction method, an alternative approach is required. Surprisingly, the inventors have also observed that dialysis of aqueous quinoa saponin extracts is a relatively inefficient purification step with only modest reduction in nonsaponin components. The approach of Mizui et al. [Mizui, F., et al. *Chem. Pharm. Bull.*, 36:1415 (1988); Mizui, F., et al. *Chem. Pharm. Bull.*, 38:375 (1990)] is complicated, involving multiple chromatography steps with low yields.

Prior art for the extraction of triterpene saponins from whole plants or seeds also includes a number of different solvent systems including acetone, diethyl-ether and ethyl acetate (Tanaka, O & Yata, N., U.S. Pat. No. 4,501,734). Surprisingly, the inventors of the present invention have found that only a narrow range of solvents can effectively extract saponins from quinoa bran.

Prior art for the purification of triterpene saponins from other whole plants or seeds includes a number of different procedures. For example, Combier, H. et al., (U.S. Pat. No. 4,335,113), teach that saponins can be extracted from an aqueous solution by n-butanol/benzene mixture after prior extraction with ethyl acetate. These researchers also teach that saponins can be purified by successive chromatography on silica gel ($CHCl_3:CH_3OH:H_2O$; 65/25/10 to 50/40/10 v/v/v) and reversed phase liquid chromatography (RP-HPLC) ($CH_3OH:H_2O$). Tanaka, O & Yata, N. (U.S. Pat. No. 4,501,734) also teaches that saponins can be purified by sequential extract of an alcoholic extract with n-hexane and ethyl acetate, prior to extraction of the saponins into n-butanol followed by column chromatography on silica gel chromatography using combinations of ethyl acetate, chloroform, n-butanol, methanol, ethanol and water as eluants. Surprisingly, but not unexpectedly since (Tanaka, O & Yata, N. U.S. Pat. No. 4,501,734) reported that ethyl acetate could be used to extract saponins, the inventors have observed that ethyl acetate will extract some saponins from an aqueous solution of quinoa saponins. The impracticability of such an approach is illustrated by recovery of only 5% of the n-butanol fraction as purified saponins. Combier, H. et al., (U.S. Pat. No. 4,335,113) also teach that the saponin containing butylic soluble component of the hot methanolic extract of Chrysanthellum sp. can be treated with activated charcoal, however no effect of the activated charcoal on saponin content or purity was shown.

Surprisingly the inventors have repeatedly observed that n-butanol and other higher alcohols are selective in their ability to recover quinoa saponins from the aqueous extracts derived from quinoa and also that recovery of saponins in the water immiscible higher alcohol fraction is surprisingly inefficient.

Kensil et al. (WO 88/09336, U.S. Pat. No. 5,057,540, Oct. 15, 1991) describe a process in which *Quillaja saponaria* bark is extracted with water, dialysed and the resulting extract lyophilized. The saponins are solubilized from the resulting powder with methanol and subjected to silica gel chromatography and/or RP-HPLC. This process was however only conducted on samples of less than 2 grams. When applied to quinoa extracts the inventors have observed little value in the dialysis step and observed that relatively little of the quinoa saponin can be resolubilized in methanol. Dorn (U.S. Pat. No. 3,883,425, May 13,1975) describes a process in which aqueous commercial saponin preparations (5 to 40% w/v) are freed from antibacterial toxins (undefined low molecular weight compounds) by passage over ultrafiltration membranes with molecular weight exclusion limits ranging from 500 to 30,000 in which losses of saponins to the permeate are claimed to be 5% or less except for the 30,000 MWCO membrane in which case the losses were reported to be 7.5%. Surprisingly the inventors find that crude quinoa saponin powders obtained from aqueous alcohol extracts of quinoa bran do not readily dissolve in water to form high molecular weight micelles. Not unexpectedly, the presence of even a small amount of alcohol appears to prevent the formation of high molecular weight micelles.

When the prior art was applied to the extraction and purification of saponins from quinoa or quinoa bran, the yield of total saponins was either significantly lower than could be achieved by the technology described herein and/or resulted in only selective recovery of some of the saponins present.

Sapogenins

Approaches for the isolation and purification of sapogenins have also been described in prior art including the isolation of oleanolic acid from *Diospyros kaki* (Liu, Y. U.S. Pat. No. 5,086,043, Feb. 4, 1992), however these methods are not applicable to quinoa seed and quinoa bran which contain three different sapogenins (Oleanolic acid, hederagenin and phytolaccagenic acid).

Loken (U.S. Pat No. 3,895999, July 22, 1975, U.S. Pat. No. 3,510,400) teaches that the preferred hydrolysis conditions for the generation of sapogenins is hydrolysis of an aqueous extract in the pH range 1.0 to 2.5 at temperatures in the range of 110°–145° C. followed by partial neutralization to pH 5–6. Surprisingly the inventors have determined that by conducting the hydrolysis in an aqueous alcohol environment the temperatures required are reduced to the boiling point of the aqueous alcohol solvent, typically 75–80° C., without significantly extending the hydrolysis time, thus representing a significant reduction in cost and removing the requirement for a pressure vessel. Prior art for the hydrolysis of triterpene sapogenins to their corresponding sapogenins describes only analytical approaches, typically 1.5% $H_2SO_4$ at 70° C. for 20 h (Solvent not defined).

Other traditional approaches to recovery of sapogenins include that described by Rajasekaran, M., et al., *J. Ethanopharmacol* 24:115,1988, who teach that oleanolic acid can be recovered from flowers of *Eugenia jambolana* by refluxing with 95% ethanol and chromatography of the benzene soluble portion of the extract on silica gel eluted with chloroform/methanol. Umehara, K., et al., *Chem. Pharm. Bull.* 40:401, 1992, also describe a similar process involving methanol extraction of cloves (*Syzygium aromaticum*) and subsequent solvent partitioning and silica gel chromatography. In this procedure when solvent partitioning is used to affect separation, the sapogenins of interest were distributed between the benzene and the methanol partitions. This is clearly not desirable in a commercial recovery process. It is also not apparent from their publication what form the oleanolic acid occurs in the clove (saponin or sapogenin). Singh, G. B., et al., *J. Pharm. Pharmacol.* 44:456,1992, describe a process for recovery of oleanolic acid from *Luffa cyllndrica* seed in which the saponins were extracted with methanol and oleanolic acid liberated by acid hydrolysis. The crude oleanolic acid was washed exhaustively with acetone and pure oleanolic acid recovered by recrystallization from ethanol. These approaches are not practical for large scale production of sapogenins and are impractical for plants that contain mixtures of sapogenins.

There is therefore a need for a simple practical process for preparation and recovery of highly purified saponins and sapogenins from quinoa that is effective on a commercial scale.

Definitions

It is felt that the following definitions may assist with the understanding of the description of the present invention.

By "saponin" is meant a compound consisting of a triterpenoid of oleanane structure and one or more glycosides, the glycosides being bound to the triterpenoid at the 3 position and/or at the 28 position.

The term "glycoside" is intended to mean all sugars including glucose found naturally in quinoa including arabinose, glucose, galactose, xylose and glucuronic acid.

By "sapogenin" is meant the triterpenoid alone without glycosides attached at either the 3 or the 28 position.

By "quinoa bran" is meant the bran obtained in a commercial mill used to de-bran quinoa for human consumption.

Some standard abbreviations used in connection with the present invention include:

HPLC—high pressure liquid chromatography (suitable apparatus for this includes (1) Waters Corporation Model 2690 Separations module (Alliance) with a 996 PDA detector; and (2) Hewlett Packard Model 1090 hplc system);

TFA—trifluoroacetic acid;

ELSD—evaporative light scattering detector;

GLC—gas liquid chromatography;

RP—reversed phase;

MWCO—molecular weight cut-off; and

SPE—solid phase extraction (suitable apparatus includes Pharmacia Model Process Stack Column PS 370, pump Spectra/Chrom Macroflow pump (head model 7090-42), resin Waters preparative C18 125A bulk packing 55–102 $\mu$m).

BRIEF SUMMARY OF THE INVENTION

An object of the present invention is to provide a process of extraction of saponins (and ultimately sapogenins) from quinoa that can be operated on a commercial basis.

According to one aspect the present invention, there is provided a process for commercial extraction of saponins from quinoa, comprising: contacting a saponin-containing part of a quinoa plant with an aqueous alcohol solution containing an alcohol selected from the group consisting of methanol and ethanol to form a saponin-containing solution and an extracted solid residue, removing the alcohol from the saponin-containing solution to leave a saponin-containing aqueous solution, and evaporating water from the saponin-containing aqueous solution to produce a saponin-containing product.

According to another aspect of the invention, there is provided a process of producing sapogenins from corresponding saponins obtained by extraction from a quinoa plant, comprising: obtaining a solution of saponins in an aqueous alcohol, adding a strong (preferably 1–3.5 N) acid to the solution to hydrolyze the saponins to form corresponding sapogenins that precipitate out of the solution as a precipitate, recovering the precipitate, and decolorizing the precipitate by forming a slurry of the precipitate with a solution of an aqueous base to form a decolorized sapogenin product.

The aqueous alcohol solution used for the initial extraction of the saponins from the plant parts preferably contains 40 to 80% alcohol by volume. Amounts above and below this range tend to result in the extraction of significantly less of the saponins and tends to result in an uneven pattern of extraction of the different individual saponins present in the plant parts. In.fact, the range of 50 to 75% alcohol is more preferred for these reasons, and the most preferred range is 50 to 60%. The optimum amount is about 50% alcohol by volume.

The ratio of extraction liquid to plant parts (e.g. bran) used for the extraction is preferably at least 8:1 v/w, more preferably at least 10:1. At smaller ratios of liquid to solid, the mixture may be too stiff to stir. When bran or quinoa flour are employed as the starting materials for extraction, there is a particular tendency for the mixture to become too thick and stiff as the plant material absorbs liquid and tends to swell. In these cases, the 10:1 ratio is the preferred minimum. As for maximum ratios of liquid to solid, there is generally no advantage in using more than 30:1 or even 15:1. As more liquid is added, more has to be removed in subsequent steps, but there is usually no significant increase in rates of extraction. The preferred ratio is therefore 10–15:1.

After extraction, the alcohol component is removed from the extraction liquor. While this can be done by any means, it is most desirable to use flash evaporation. Flash evaporation is a technique known in preparative chemistry for the rapid removal of a volatile component from a liquid mixture. The volatile liquid is removed from solution by rapid conversion to a vapor phase by creating a thin film of the solution over a large surface area under reduced pressure often accompanied by an increase of temperature of the solution above ambient but less than the boiling point of the solution at atmospheric pressure. The actual thickness of the film and the area over which it is applied is chosen to provide optimum evaporation and ease of use, but evaporation may be substantially instantaneous (hence the name "flash" evaporation). Flash evaporation avoids the prolonged use of high temperatures that may degrade the intended product and has the ability to remove almost all of the alcohol component (which makes the remaining solution suitable for the preferred practice of spray drying employed in the next step. The alcohol may be recovered from this step and re-used in the extraction process.

For the removal of water from the extraction liquor, spray drying is preferred, although other techniques could be employed. Spray drying is a known technique regularly used in preparative chemistry and the food processing industry in which a fine spray of droplets of the liquid is introduced into a moving gas (usually air) flow to cause loss of moisture from the droplets). The gas is often heated, e.g. it may have an inlet temperature in the range of 80–150° C. and an outlet temperature that is lower, typically 50–100° C. (actual temperatures are usually machine-dependent and are adjusted to achieve optimum results). Spray drying is rapid and again may avoid the prolonged exposure of the product to high temperatures. The dry product resulting from spray drying is obtained in the form of a fine powder that is easy to collect, manipulate, store and re-dissolve.

The extraction process of the invention is preferably carried out on a commercial variety or cultivar of quinoa using a dry (non-green) part, and most preferably a bran product obtained by dry milling to remove seed coats from commercial quinoa grain. Quinoa bran is commercially available and inexpensive (virtually a waste product) resulting from the treatment of quinoa seed to form a consumable flour. Quinoa bran is rich in saponins (the bran contains approximately 50 times more saponin than could be recovered by washing the whole grain or extracting ground seed) and can be obtained by dry milling of high saponin content quinoa. However, if desired, other (preferably not green) parts of the quinoa plant may be used as starting materials for the saponin extraction, e.g. whole seeds, ground seeds, seed coats or quinoa flour.

The saponin content of the quinoa starting material (e.g. bran) and the ensuing fractions can be monitored, for example, by HPLC analysis of a filtered 50% (v/v) ethanol or methanol extract of the bran by chromatography on C-8 or C-18 RP columns eluted with a 0.05% Trifluoroacetic acid (v/v) (TFA) in water:methanol gradient, or a 0.05% TFA in water:acetonitrile gradient. Saponins in the samples are detected by Evaporative Light Scattering Detection (ELSD) using, for example, Model PL-EMD 960 from Polymer Laboratories (settings: atten 1; air temp. 90° C.; air flow 3.7 l/m). Acetic acid (1%) can be used in place of TFA and chromatographic separation can be achieved by isocratic elution. The sapogenin content of extracts and samples derived by hydrolysis can also be determined using the same chromatographic procedure.

A substantially enriched dry saponin fraction is obtained by extraction of the bran with 50% v/v aqueous alcohol (methanol or ethanol), evaporation of the alcohol (methanol or ethanol) and spray drying of the concentrate to give a powder. Surprisingly, extraction of bran or seed with aqueous alcohol yields an extract that contains more than twice the amount of saponin than extraction with either water or pure alcohols alone.

Also surprisingly, both water and alcohol, when used individually, differentially extract saponins (of which there are usually three main kinds) from the bran with the result that the saponin composition of the pure alcohol extract is substantially different from the aqueous alcohol or aqueous extracts. In the product of the process of the present invention, the saponin profile of the bran extract is substantially the same as that of the quinoa starting material, e.g. quinoa seed, which leads to greater extraction efficiency and yield.

Surprisingly the inventors have also observed that other extracting solvents and conditions described in the prior art as being suitable for extraction of saponins are largely ineffective in removing saponins from quinoa bran or whole seed.

The saponin content of the aqueous alcohol extract can be further increased by passage over a 1000 MWCO spiral wound ultrafiltration membrane (e.g. an Amicon Model S3Y1 spiral wound ultrafiltration cartridge) without significant alteration to or loss of the saponin composition. This concentrated saponin fraction where the saponin content is in the range of 85–90%, can then be further purified in a liquid state or reduced to a dry state. Individual saponins are recovered by a combination of reversed-phase solid phase extraction and preparative reversed-phase HPLC (e.g. using Waters Corporation Model Prep 4000 with a 486 tunable wavelength detector). Alternatively, the aqueous alcohol extract containing saponins can be fractionated directly by a combination of reversed-phase solid phase extraction and preparative reversed-phase HPLC, however this is less efficient in the absence of the membrane pretreatment.

A concentrated solution of the sapogenins can be obtained by acid hydrolysis, for example using 450 mL concentrated HCl per 3 L of the aqueous alcohol extract (e.g. 50% v/v ethanol) under reflux (e.g. for 6 hours). The hydrolysate is allowed to cool resulting in the formation of a precipitate which is recovered by filtration. The precipitate is slurried in water (e.g 2 L) and the resulting slurry is adjusted preferably to pH 10 with a base (NaOH). The sapogenins precipitate from the basic solution as off-white crystals and are recovered by filtration. The resulting crystalline precipitate is washed with dilute acid (e.g. 2 L of 1.0 N) and distilled water until the effluent is clear. Surprisingly, the precipitate is essentially free from coloured impurities, where as precipitated sapogenins obtained under neutral or acidic conditions are dark brown in colour. The precipitate containing the sapogenins may then be air-dried and can be further refined by recrystallization.

The individual sapogenins may be recovered from this mixture, e.g. by preparative HPLC using reversed-phase adsorbents. The purification can also be achieved on a large scale by selective desorption from a reversed-phase solid-phase extraction cartridge eluted with a step gradient of aqueous methanol. Preparative HPLC and systems such as simulated moving bed chromatography are frequently in commercial use for recovery of high value solutes from solutions. The sapogenins may be further purified by recrystallization from hot 95% alcohol.

BRIEF DESCRIPTION OF THE SEVERAL VIEWS OF THE DRAWINGS

FIG. 5A shows the original extract; FIG. 5B shows the n-butanol phase; and FIG 5C shows the remaining water phase.

FIG. 9A shows Phytolaccagenic acid; FIG. 9B shows Hederagenin (containing some phytolaccagenic acid); and FIG. 9C shows Oleanolic acid. Waters Novapak C-18 (3.9×150 mm, 4 μm) eluted with a linear gradient of aqueous 0.05% TFA:acetonitrile containing 0.05% TFA (T=0,% $CH_3CN$=5; T=20,% $CH_3CN$=95) at a flow rate of 1 mL/min and ELSD detection.

DETAILED DESCRIPTION OF THE INVENTION

Throughout the description of the invention reference is made to certain publications including scientific articles and patents or patent applications. It is intended that each of these publications be incorporated by reference when referred to in the specification.

Unless defined otherwise all technical and scientific terms used have the same meaning as commonly understood by one of ordinary skill in the art to which this invention belongs.

Although any methods and materials similar or equivalent to those described herein can be used in the practice or testing of the present invention, the preferred methods and materials are described herein.

As this process is operated on an intermittent basis, and the quinoa seed may be from different cultivars, the composition of the bran used in the following examples is not uniform in terms of total saponin content, although all three main saponins were always present in approximately equal proportions.

General Overview

An unexpected discovery was that extraction of triterpenoid saponins from quinoa grain and quinoa bran is highly influenced by the solvent used and the conditions applied to the extraction, and that application of the prior art to the concentration and purification of the saponins and their corresponding sapogenins yielded disappointing results which would have a significant impact on the commercial recovery of these compounds from quinoa bran. The present invention describes a simple and efficient process for the recovery of saponins and sapogenins from quinoa grain and/or quinoa bran and for the fractionation and purification of these compounds to states of purity up to and including greater than 98% pure.

Figure 1A:
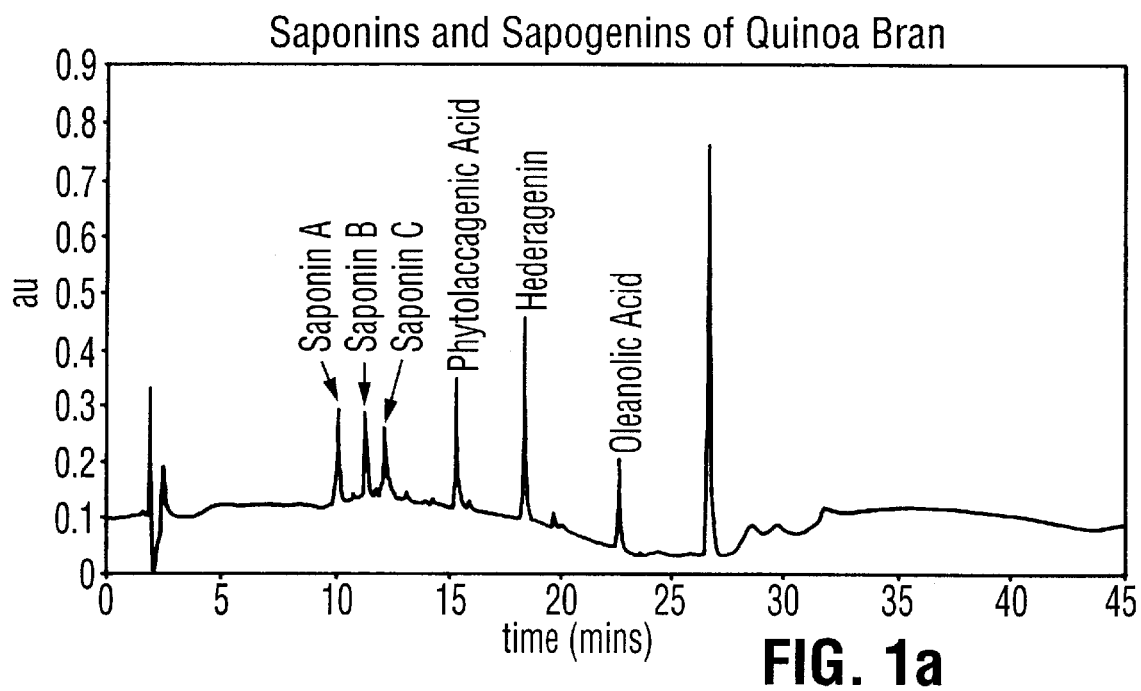
FIGS. 1A and 1B depict the RP-HPLC profile of the partial hydrolysis of the aqueous ethanol extract of quinoa bran illustrating the partial conversion of the three principle saponins (Saponins A, B and C) into their corresponding sapogenins phytolaccagenic acid, hederagenin and oleanolic acid. Chromatography was performed on a Symmetry C-18 column (Waters) (3.0×150 mm, 4 $\mu$m) eluted with a linear gradient of aqueous 0.05% TFA:acetonitrile containing 0.05% TFA (T=0,% $CH_3CN$=5; T=20,% $CH_3CN$=95) at a flow rate of 0.4 mL/min and the saponins and sapogenins detected by UV (FIG. 1A) or ELSD (FIG. 1B).
Figure 1B:
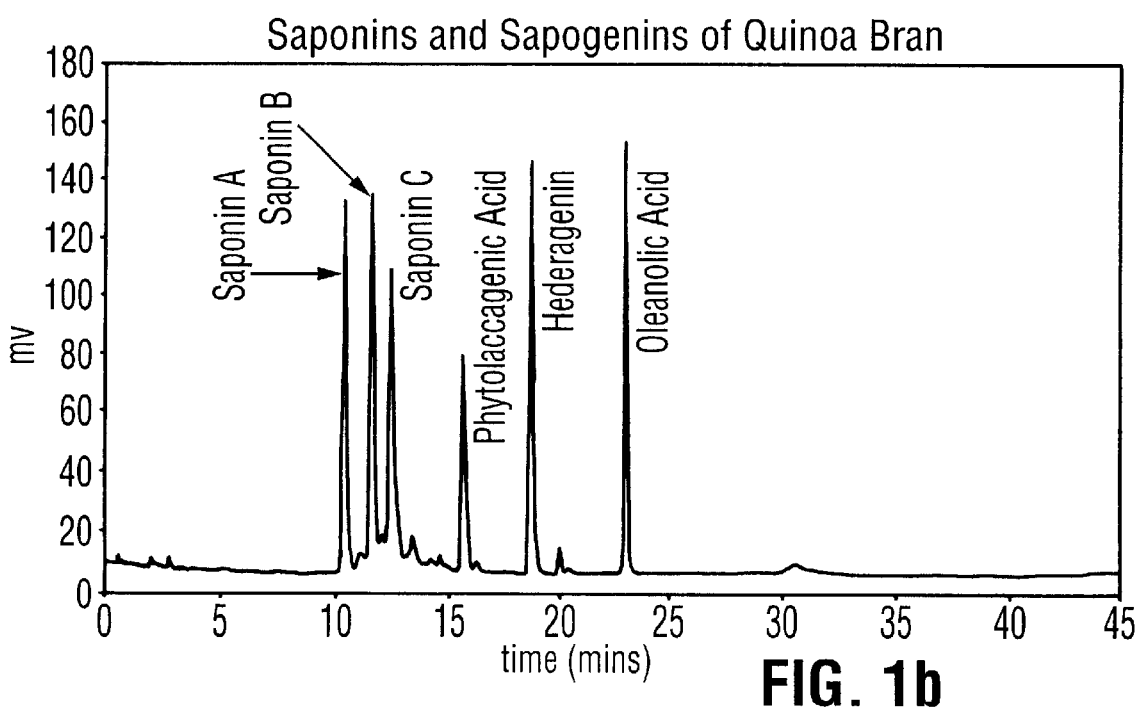
Figure 2A:
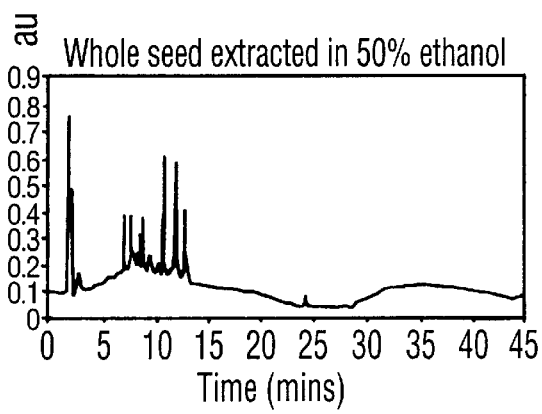
FIGS. 2A, 2B, 2C, 2D, 2E and 2F depict the RP-HPLC profiles of the 50% v/v ethanol extracts of: whole quinoa seed—210 nm UV (FIG. 2A); whole quinoa seed—ELSD (FIG. 2B); whole ground quinoa seed—210 nm UV (FIG. 2C); whole ground quinoa seed—ELSD (FIG. 2D); quinoa bran fraction—210 nm UV (FIG. 2E); and quinoa bran fraction—ELSD (FIG. 2F). All samples were extracted for 4 hr at 50° C.
Figure 2B:
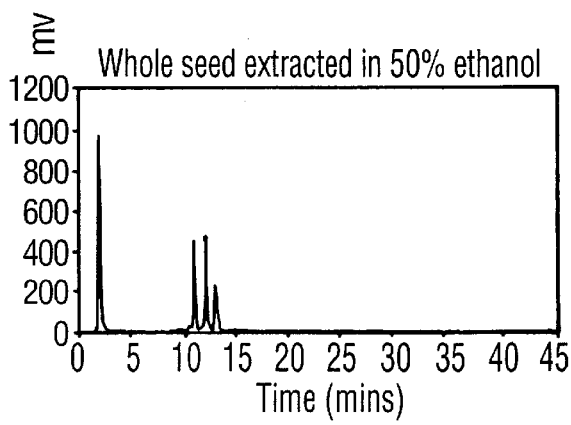
Figure 2C:
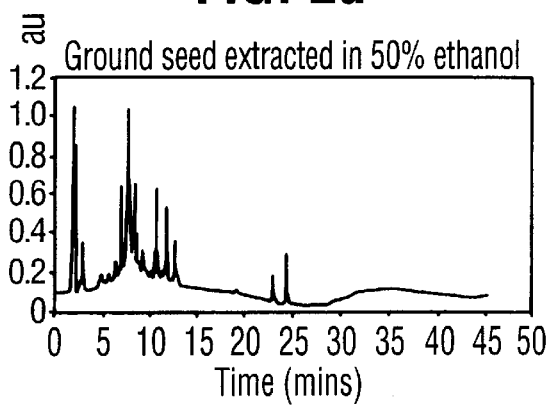
Figure 2D:
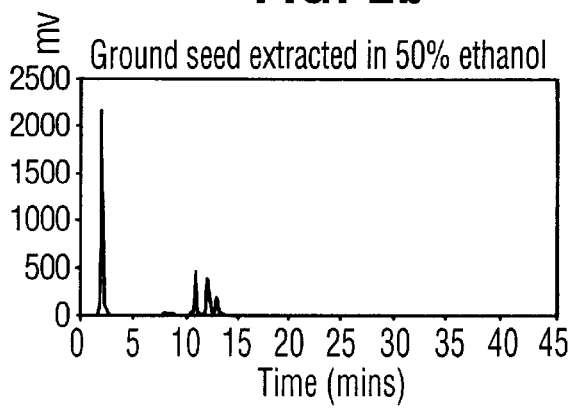
Figure 2E:
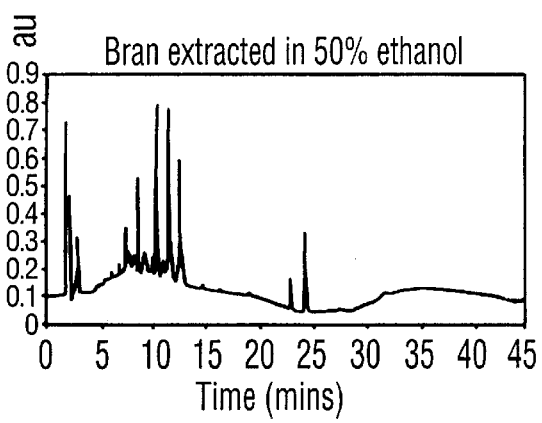
Figure 2F:
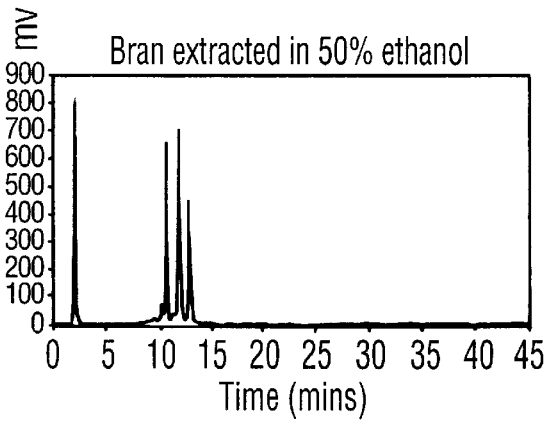

An important aspect of the present invention is the development of an analytical RP-HPLC chromatographic separation that enabled monitoring and also the simultaneous quantization of both saponins and sapogenins in quinoa extracts. This technique can best be illustrated by reference to FIG. 1, which depicts the chromatography of the partially hydrolyzed aqueous ethanol extract of quinoa bran. In this figure the saponins and their corresponding sapogenins are clearly resolved from each other. Using this analytical technique, the inventors were able to follow the precise distribution of the saponins and sapogenins during the extraction and purification process.

The effects of lower alcohols and combinations of lower alcohols and water and water alone, were investigated for their effectiveness in extracting saponins from the bran. Surprisingly, water, which is widely and traditionally used for extraction of saponins, was not particularly efficient, nor were pure alcohols. Aqueous alcohols in the range 50–75% v/v were found to be the preferred solvents, yielding significantly higher amounts of saponins from the bran and in proportion to that found in the whole grain. An added benefit of aqueous alcohol extraction was the concentration effect that occurred when the alcohol was removed by flash evaporation or an alternative method such as rising film evaporation. A surprising additional benefit was obtained in that the aqueous alcohol extracts did not require preservation with sodium azide as taught in the prior art of Kensil (WO 88/09336, U.S. Pat. No. 5,057,540, Oct. 15, 1991).

A number of options for purification of the quinoa saponins were investigated. Surprisingly, when the process described by Kensil et al. (WO 88/09336, U.S. Pat. No. 5,057,540, Oct. 15, 1991) was applied to a sample of quinoa bran only 27.4% of the saponins in the aqueous extract were found in the methanol soluble fraction and the saponin profile differed significantly from that of the initial extract. The methanol soluble fraction was enriched in saponin A and contained proportionally less of saponin C in relation to the aqueous extract (Table 2). The use of a 15,000 MWCO ultrafiltration membrane was also examined for possible utility in removing protein from the saponin extract. Surprisingly, it was determined that only approximately ⅓ of the saponin in the extract was able to pass through the 15,000 MWCO membrane even with repeated dilution of the retentate. Thus the use of a 15,000 MWCO membrane served only to dilute the saponin content of the permeate and resulted in the distribution of the saponins into both fractions. The use of a 300 MWCO ultrafiltration membrane, however, proved useful in that less than 1% of the saponin passed through this membrane and the retentate was highly enriched in saponins.

The use of silica gel chromatography and semi-preparative HPLC as described in prior art (Kensil; WO 88/09336, U.S. Pat. No. 5,057,540, Oct. 15, 1991) is clearly not practical on a large scale, employing mixed solvents that are difficult to recycle and has not been demonstrated to be practical on a commercial scale. As is demonstrated in examples to follow, the approach described in the prior art would only be applicable to the 27% of the quinoa saponin that could readily solvated in methanol.

Having discussed the short comings of the prior art and described our invention in general terms, the full impact of our invention will be illustrated in the following examples. These are given by way of differentiating the present invention from aspects of the prior art and should not be taken in any way to limit the scope of the present invention.

EXAMPLES

Example 1
Optimization of Saponin Extraction

Quinoa bran obtained from the commercial de-branning of quinoa grain was extracted with the following solvents: water, 50% v/v methanol, 50% v/v ethanol, 95% ethanol and methanol. The resulting extracts were filtered and analyzed by RP-HPLC. The saponin content was determined by chromatography on a Waters Symmetry C-18 column (3.0× 250 mm, 5 $\mu$m) eluted with a linear gradient of aqueous 0.05% v/v TFA:acetonitrile (T=0,% $CH_3CN$=5; T=25,% $CH_3CN$=95) at a flow rate of 0.4 mL/min, with UV detection at 210 nm and evaporative light scattering detection (ELSD). Waters Novapak C-18 (3.9×150 mm, 4 $\mu$m) eluted with a linear gradient of aqueous 0.05% trifluoroacetic acid:acetdnitrile containing 0.05% TFA (T=0,% $CH_3CN$=5; T=20,% $CH_3CN$=95) at a flow rate of 1 mL/min. Quantitation of saponins was initially by external standards using the saponin hederacoside C (Indofine) as the external standard. However, subsequent calculations of saponin content employed purified quinoa saponins purified in our laboratories as standards. The composition of the saponin extracts of quinoa is shown in FIG. 2. The saponin profile of the 50% v/v ethanol extract of the bran was also compared to the 50% v/v ethanol extract of the whole or ground seed (FIG. 2). The saponin profile was essentially identical for all three extracts (FIGS. 2b,d,f), however the whole seed and whole ground seed extracts contained significantly more UV absorbing impurities (FIGS. 2a, c) than the bran extract (FIG. 2e), and which additionally would have to be removed in the purification process. The bran was also the preferred source on the basis of the significantly higher concentration (50×) of saponin in the bran compared to whole or ground seed (Table 1).

TABLE 1

Extraction of saponins from quinoa seed, ground seed and bran.
The samples were extracted in 50% v/v ethanol at 50° C. Values in the table are for 1 gm of sample (mg saponin/g)

| Sample | Total Saponin | Saponin A | Saponin B | Saponin C |
|---|---|---|---|---|
| Bran | 230.06 | 75.89 | 87.50 | 66.67 |
| Whole seed | 5.24 | 1.99 | 1.91 | 1.33 |

TABLE 1-continued

Extraction of saponins from quinoa seed, ground seed and bran.
The samples were extracted in 50% v/v ethanol at 50° C. Values in the table are for 1 gm of sample (mg saponin/g)

| Sample | Total Saponin | Saponin A | Saponin B | Saponin C |
|---|---|---|---|---|
| Ground seed | 3.76 | 1.47 | 1.29 | 1.00 | n.b. There was sufficient water in the extracting solvent to partially swell the starch in the ground seed, reducing the efficiency of saponin extraction in the slurry.

Figure 3:
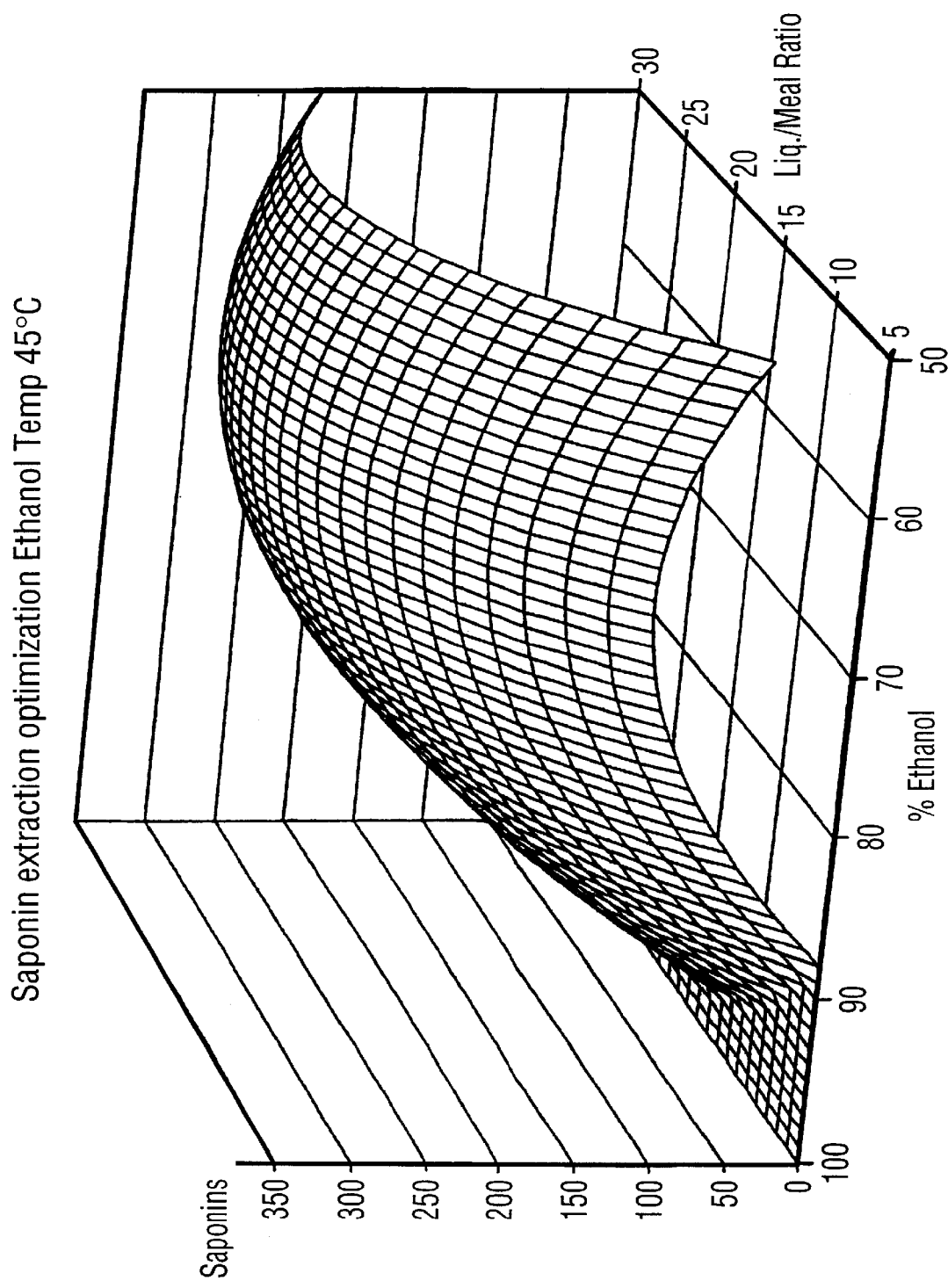
FIG. 3 depicts the surface response curve for extraction of saponins from quinoa bran. The figure shows the saponin content of extracts obtained at 45° C. by varying the ethanol concentration in the extraction medium from 50% to 100% at liquid to solids ratios of 5:1 to 30:1.
Figure 4A:
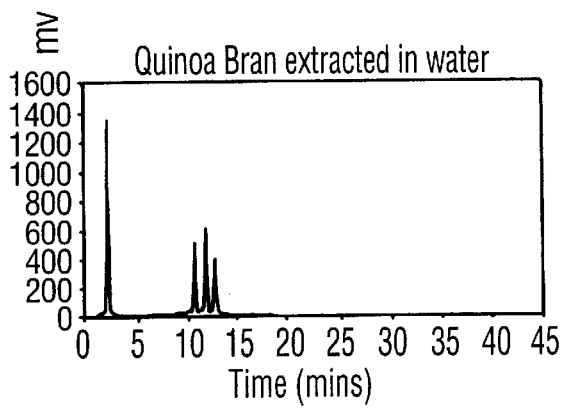
FIGS. 4A, 4B, 4C, 4D, and 4E depict the RP-HPLC analysis of the saponin extracts obtained by extraction of quinoa bran with: water (FIG. 4A); 50% v/v methanol (FIG. 4B); methanol (FIG. 4C); 50% v/v ethanol (FIG. 4D); and ethanol (FIG. 4E). The chromatograms show the ELSD response (mV) after chromatography on a Symmetry C-18 column eluted with 0.1% v/v aqueous TFA:acetonitrile gradient. The saponins were detected using ELSD.
Figure 4B:
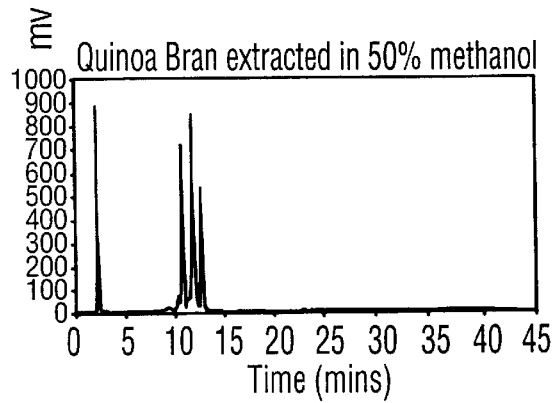
Figure 4C:
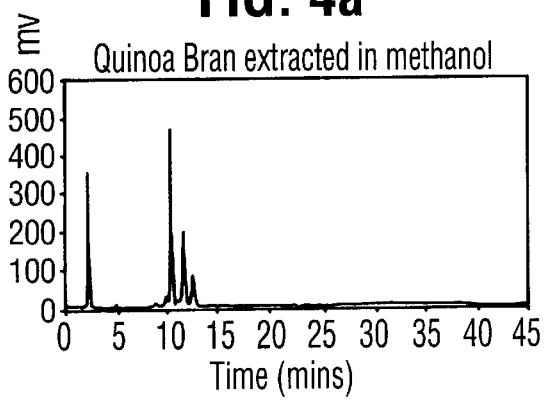
Figure 4D:
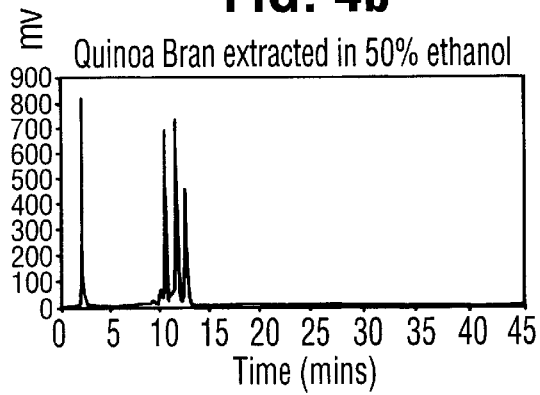
Figure 4E:
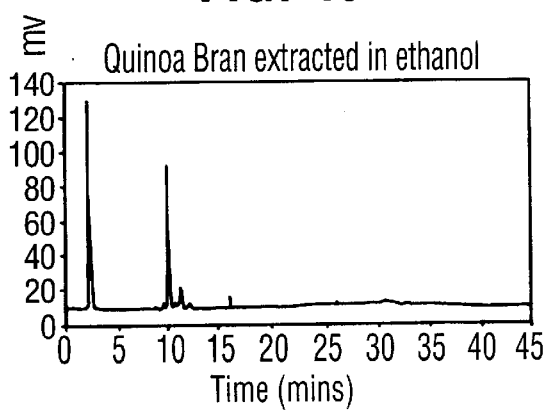

The optimal extraction conditions for the recovery of saponins from quinoa bran was determined from a series of optimization studies. The effects of varying extraction temperature (25° C. to 65° C.) was found to have little effect on recovery of saponins, however both liquid to solids ratio and the alcohol content of the extracting solvent had highly significant effects on extraction efficiency (FIG. 3.). The saponin profile of the extracts obtained under the different extraction conditions was examined by RP-HPLC. Surprisingly, not only does the composition of the extracting solvent effect the extraction efficiency but it also effects the composition of the extract. The 100% methanol extract, a commonly used extraction solvent, gave the lowest extraction efficiency while preferentially extracting only one of the three main saponins (FIG. 4.).

Example 2
Pilot Plant Scale Extraction of Saponins from Quinoa Bran

To establish the practicality of large scale extraction of saponins, Quinoa bran (100 kg) obtained from the commercial de-branning of quinoa was contacted with 50% aqueous ethanol (v/v) (liquid to solids; 10:1) in a stainless steel kettle for 4 hours under stirring. The aqueous ethanol was decanted from the solid residue using a Westphalia decanting centrifuge, and replaced with a similar volume of clean solvent for a further 4 hours. The liquid extract was again separated from the solid residue by centrifugation in a Westphalia decanting centrifuge and the resulting liquid extract combined with the first extract. The combined aqueous alcohol extracts were filtered through a plate and flame filter to polish the extract. The filtered extract was reduced to the aqueous phase by flash evaporation on a APV evaporator. The resulting aqueous extract was spray-dried to yield 27 Kg of dried extract. The saponin content of the spray-dried powder was determined to be 78% comprised of 24.6% saponin A, 39.7% saponin B and 35.5% saponin C.

Figure 5A:
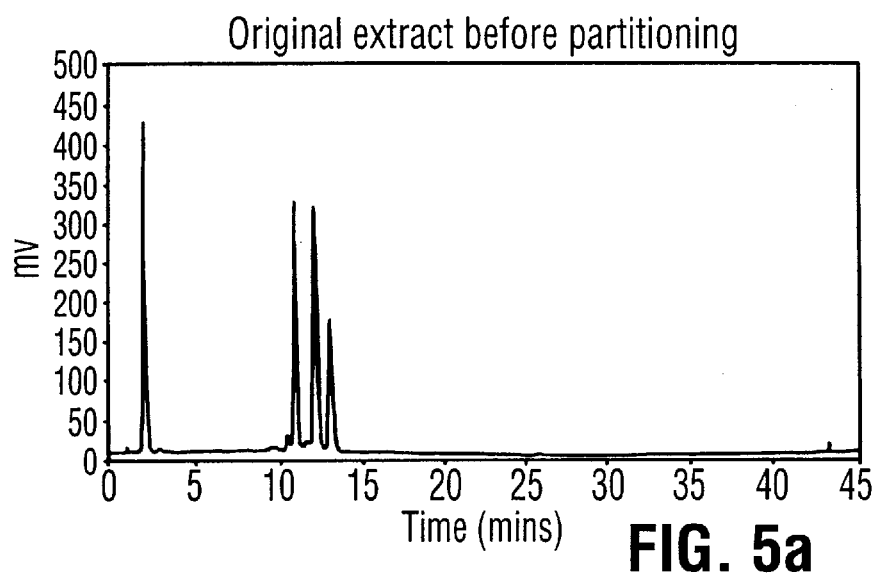
FIGS. 5A, 5B and 5C depict the effects of partitioning quinoa saponins between water and n-butanol. A 50%(v/v) aqueous ethanol extract of quinoa bran was reduced to a powder and reconstituted in water prior to partitioning against n-butanol. Chromatography was performed on a Symmetry C-18 column eluted with 0.05% (v/v) aqueous TFA:acetonitrile gradient and the saponins detected using ELSD.
Figure 5B:
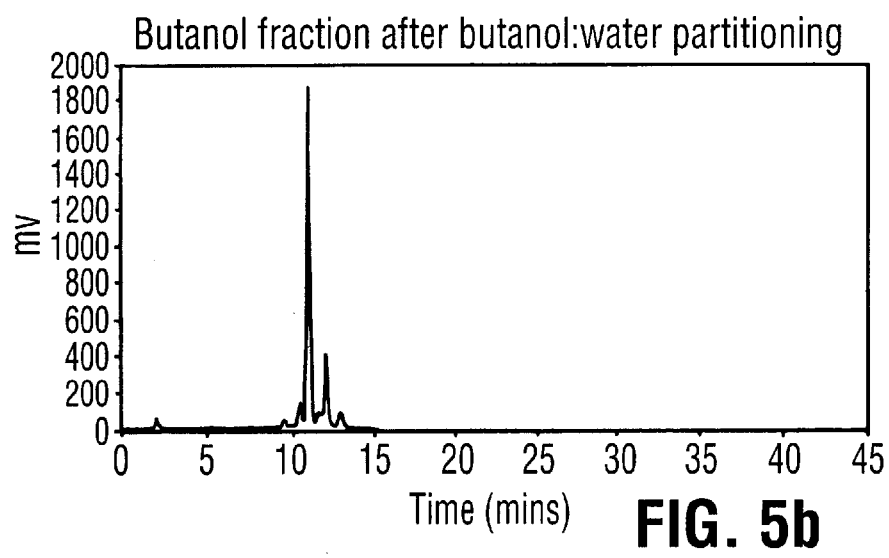
Figure 5C:
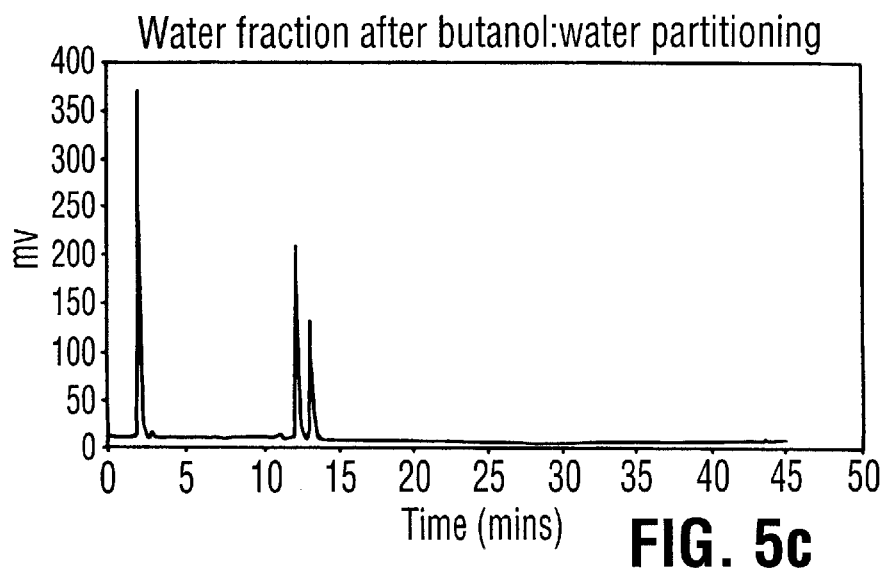

Example 3
Comparative Evaluation of the Prior Art for the Purification of Saponins The prior art describes a number of procedures for purification of saponins. These procedures were evaluated in a comparative study.

a) Partition of Saponins Between Aqueous Extracts and a Water Immiscible Solvent A common method for purification of saponins involves extraction of the saponins from an aqueous solution into a n-butanol solution. Aqueous extracts of quinoa bran (2.52 g of bran in 50 mL water, for 4 hr at 50° C.) were subjected to n-butanol partition extraction and the aqueous and n-butanol fractions analyzed by RP-HPLC. n-Butanol was found to be relatively inefficient for extraction of quinoa saponins from the aqueous phase. After 4 exchanges with n-butanol, 58% of the total saponins still remained in the aqueous phase. The experiment was repeated for saponin extracts obtained by extraction with 50% v/v methanol, 50% v/v ethanol and 100% methanol. In these experiments, the alcohol was first removed by evaporation under reduced pressure and the resulting extract reconstituted in water. In all cases between 33 and 62% of the total saponins remained in the aqueous phase after n-butanol extraction. Surprisingly, the RP-HPLC analysis of the n-butanol and aqueous phases revealed that the three principle saponins present in quinoa exhibited different solubilities in n-butanol. In all examples, n-butanol preferentially extracted saponin A, leaving almost none of this saponin in the aqueous phase, while almost none of saponin C was recovered in the n-butanol phase (FIG. 5). The partitioning of quinoa saponins, obtained by extraction of quinoa bran with 50% w/v ethanol, between water and high alcohol was also investigated. The 50% w/v ethanol extract was reduced to the aqueous phase and spray-dried. The resulting powder was dissolved in water (100 mL containing 500 mg of saponin powder) and extracted 3 times with 50 mL of a water immiscible higher alcohol. The organic phases were recovered and combined, reduced to dryness, reconstituted in 50% v/v methanol and analysed by HPLC. The remaining aqueous phases were also reconstituted to 50% v/v methanol and analysed by HPLC. In all cases examined (Table 2), the higher alcohols were relatively inefficient at recovering the saponins with recoveries ranging from 15% for 2-octanol to 40% for n-butanol. In all cases the saponin profile in the organic fraction did not represent the distribution observed in the crude saponin fraction, nor did they provide sufficient selectivity in extraction to be a useful purification tool. Quinoa saponin partition characteristics between water and chloroform, ethyl acetate and methyl ethyl ketone were also investigated. In all cases the water phase was extracted 3 times with the organic phase and the saponin content of the combined organic phases determined. The proportion of the saponin recovered in the organic phase was 4.4 and 6.5% respectively.

TABLE 2

Partitioning of quinoa saponins between water and a water immiscible solvent.

| Sample | Total Saponins | Saponin A | Saponin B | Saponin C |
|---|---|---|---|---|
| Original Extract 1-Octanol partition | 380 | 88 | 158 | 134 |
| Water Phase | 227 | 29 | 98 | 100 |
| 1-Octanol 2-Octanol partition | 104 | 60 | 29 | 15 |
| Water Phase | 306 | 61 | 127 | 118 |
| 2-Octanol Hexanol partition | 56 | 24 | 20 | 12 |
| Water phase | 270 | 21 | 122 | 127 |
| Hexanol n-Butanol partition | 112 | 73 | 26 | 13 |
| Water phase | 214 | 31 | 96 | 87 |
| n-Butanol | 145 | 80 | 39 | 26 |

TABLE 3

Effect of membrane filtration (15,000 MWCO) and methanol solubilization on saponin recovery from aqueous quinoa extracts. Saponin yield in g.

| Sample | Total Saponins | Saponin A | Saponin B | Saponin C |
|---|---|---|---|---|
| Original Extract | 4.64 | 1.09 | 1.24 | 0.96 |
| Retentate | 3.98 | 0.88 | 1.02 | 0.77 |
| Methanol soluble | 1.27 | 0.46 | 0.25 | 0.13 |
| Methanol insoluble | 2.77 | 0.40 | 0.80 | 0.62 | b) Dialysis

Dialysis of aqueous saponin extracts is also described in the prior art. Dialysis of aqueous quinoa bran extracts using conventional dialysis membranes did not appear to offer any significant benefit. Dialysis using a 500 MWCO cellulose ester membrane (Spectra/Por CE; Spectrum Medical Industries) did not change the saponin content of the retentate or significantly alter its UV or ELSD profile. Dialysis with 1000 MWCO regenerated cellulose (Spectra/Por 6; Spectrum Medical Industries) and 3500 MWCO regenerated cellulose (Spectra/Por 3; Spectrum Medical Industries) membranes afforded a slight increase in the saponin content of the retentate. There was a reduction in some of the nonsaponin peaks in the UV-chromatograms but no significant changes in the saponin profiles by with UV or ELSD detection.

c) Membrane Filtration

Membrane filtration or ultrafiltration is a technique commonly employed in commercial practice to concentrate solutes in an extract. The crude saponin extract from quinoa was processed by passage over a membrane with a molecular weight cut-off of 15,000. Quinoa bran (100 g) was extracted with water (1 L). The aqueous extract was filtered and 250 mL of the extract was centrifuged at 10,000 rpm for 30 minutes. The supernatant was lyophilized (9.4 g) and redissolved in 30 mL of water. The pH was adjusted to less than 4 with the addition of 300 $\mu$L of 1 N acetic acid. The solution was membrane filtered over a 15,000 MWCO membrane. Both the retentate and the filtrate were recovered and lyophilized for analysis. The lyophilized retentate was extracted with methanol (3×60 mL at 60° C.) followed by centrifugation (3500 rpm, 10 minutes). The methanol extracts were combined and along with the methanol insoluble material, analyzed for saponins. Approximately 10% of the saponins present in the original extract were lost at each stage. Of the 4.64 g of saponin present in the original extract only 1.27 g (27.4%) was recovered from the methanol soluble fraction. The remaining 73% was either retained on the membrane or distributed between the permeate and the methanol insoluble fractions. The saponin profile of the methanol soluble fraction was also significantly different from the original extract (Table 3). The methanol soluble fraction was enriched in saponin A and contained proportionally less saponin C than the original extract.

Example 4

Purification of Saponins Using Techniques Described in this Invention a) Ultrafiltration of Aqueous Alcoholic Extracts Containing Saponins The saponin fraction in a 50% w/v ethanolic extract of quinoa bran can be successfully concentrated and purified directly by passage over a membrane with a molecular weight cut-off of 300. Quinoa bran (25 g) was extracted with 50% v/v ethanol (1.25 L) for 4 hours and filtered to yield 1.21 L of extract. A subsample (121 mL containing 2.861 g of saponin) was applied to a 300 MWCO membrane and filtered under positive nitrogen pressure. The filtrate (85 mL) and the retentate (30 mL) were recovered for saponin analysis. Approximately 10% of the saponin was retained on the membrane. Less than 1% of the recovered saponin was in the filtrate. 99% of the recovered saponin was in the retentate (89.7% of the applied saponin) in 25% of the original sample volume.

b) Ultrafiltration of Aqueous Saponins Extracts Containing 5% Alcohol

The 50% v/v aqueous ethanol extracts of quinoa bran can be reduced to a substantially aqueous phase (5% ethanol) prior to ultrafiltration. In this example the inventors observed that a slightly larger pore size membrane may be employed with a greater membrane flux. In this example, 150 gm of spray-dried 50% w/v ethanol extract (equivalent to 385 gm of bran) was reconstituted in 20 L of 5% aqueous ethanol, filtered to remove any undissolved particulate material and cycled over a 1000 MWCO Spiral wound membrane (Amicon S3Y1) with a permeate flow rate of 18 mL/min. The volume of saponin extract retentate was maintained at 20 L by addition of 5% ethanol to prevent precipitation on the membrane surface. The saponin extract was determined to be 77% saponin (115 gm of saponin contained in 150 gm of powder) by HPLC analysis before the ultrafiltration step and 89% saponin (83 gm of saponin in 93.3 gm of powder) in the retentate at the end of the experiment. The permeate contained 31% of the applied solids with a saponin content of 7% which was exclusively saponin A. This represented 2.6% of the applied saponin and/or 3.4% of the recovered saponin.

c) Preparative HPLC

Figure 6A:
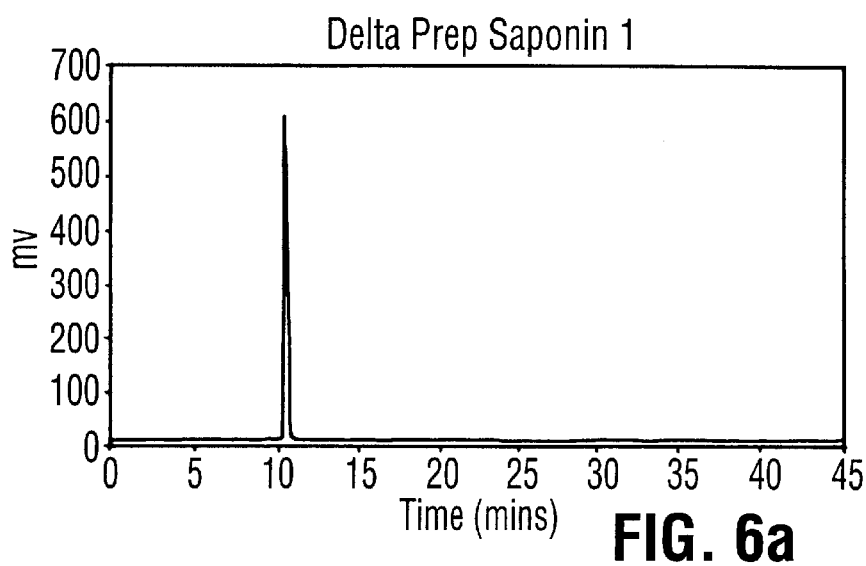
FIGS. 6A, 6B and 6C depict the RP-HPLC analysis of saponins A (FIG. 6a), B (FIG. 6B) and C (FIG. 6C) obtained by preparative HPLC chromatography of the crude concentrated saponin extract. Waters Symmetry C-18 (3.9×150 mm, 4 μm eluted with a linear gradient of aqueous 0.05% TFA:acetonitrile containing 0.05% TFA (T=0,% $CH_3CN$=5; T=20,% $CH_3CN$=95 ) at a flow rate of 0.4 mL/min. The saponins were detected using ELSD.
Figure 6B:
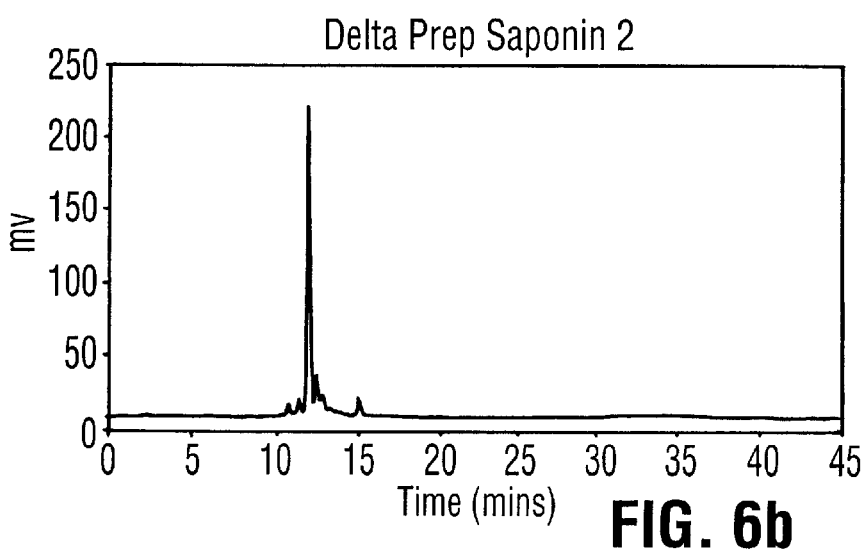
Figure 6C:
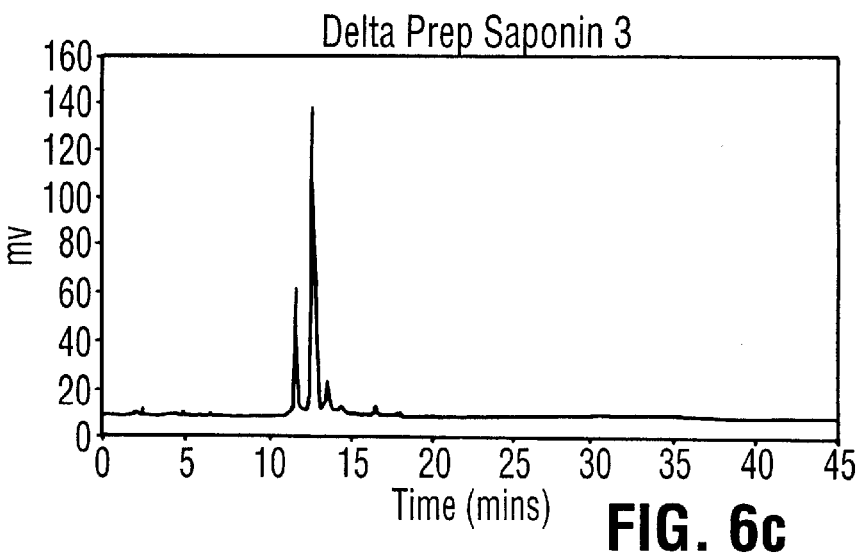

The highly enriched retentate fraction was chromatographed on a Bondapack C-18 Waters preparative column (40×310 mm) eluted with a gradient of aqueous 1% acetic acid and methanol at a flow rate of 50 mL/min (T=0,% $CH_3OH$=35; T=20,% $CH_3OH$=60; T=30,% $CH_3OH$=80; T=40,% $CH_3OH$=80). Saponin A eluted between 29 and 31 minutes (FIG. 6a), saponin B eluted between 31 and 33 minutes (FIG. 6b) and saponin C eluted between 35 and 37 minutes (FIG. 6c).

Example 5

Purification of Quinoa Saponins by Solid Phase Extraction

Quinoa saponins were separated into three major fractions, each highly enriched in one of the three most abundant saponins present in the total extract. The starting material in this example was the spray-dried powder obtained by extraction of quinoa bran with 50% w/v ethanol. The powder (200 gm) was reconstituted in 1% methanol, filtered, and applied to a solid-phase extraction cartridge (12 kg of C-18 RP resin —Waters C-18, 125 Å, 55–105 μm) preconditioned with 1% methanol. The non-retained material was washed from the column with 5% methanol and the three major saponins eluted in turn with 40% methanol.

Example 6

Figure 7:
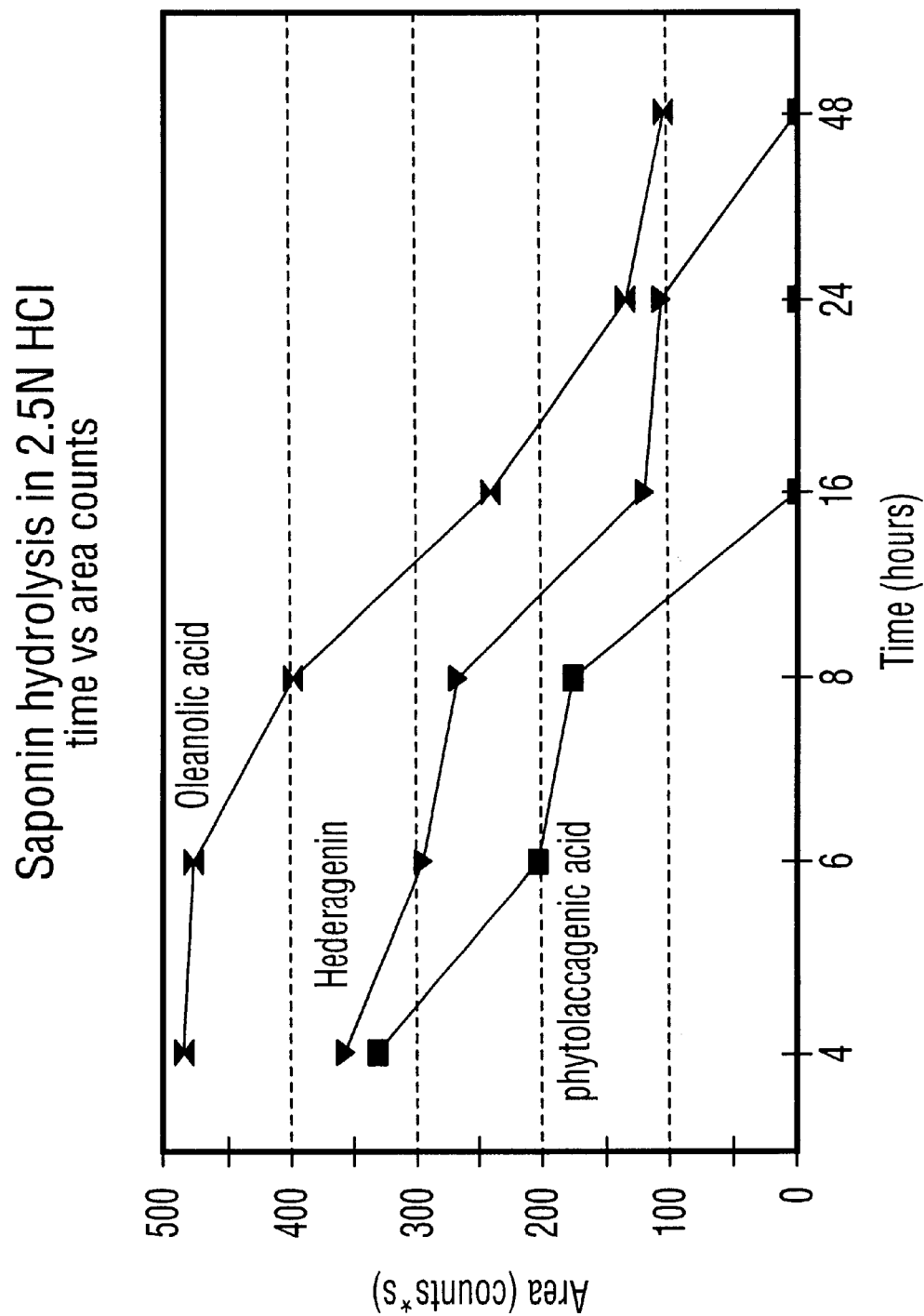
FIG. 7 depicts the effect of hydrolysis time on the yield of sapogenins from quinoa saponins. The spray-dried aqueous ethanolic extract of quinoa bran was dissolved in 50% v/v ethanol containing 2.5 N HCl. Aliquots were removed for analysis at 2 hour intervals and subjected to RP-HPLC analysis. The yield of sapogenins was determined at each time interval.

Hydrolysis of Quinoa Saponins to their Corresponding Sapogenins and Recovery as a Concentrated Sapogenin Powder Based on the prior art several different hydrolysis conditions were investigated to determine the most efficient method for cleavage of the sugars from the saponins to give the free sapogenins. Both aqueous alcoholic solutions of sulphuric acid and hydrochloric acid were found to cause effective hydrolysis of quinoa sapogenins to their corresponding sapogenins, however hydrochloric acid was found to be the preferred acid for it generated fewer artifacts. Phosphoric acid, acetic acid, sodium hydroxide and ammonia were all found to have little hydrolytic activity against quinoa saponins or to produce products other than the desired sapogenins. To determine the preferred duration of hydrolysis, the spray-dried aqueous ethanol extract of quinoa bran was dissolved in aqueous ethanol containing 2.8 N HCl. Aliquots were removed at 2 hour intervals and the concentration of the corresponding sapogenins determined by RP-HPLC. The release of the three principle sapogenins (oleanolic acid, hederagenin and phytolaccagenic acid) reached maximum levels after 4 hours of exposure to hydrolytic conditions (FIG. 7). By 6 hours, the concentration of phytolaccagenic acid and hederagenin had begun to decline and by 8 hours, the concentration of oleanolic acid had also begun to decline indicating that excessive exposure to 2.8 N HCl caused decomposition of the saponins themselves. However, for large scale production of sapogenins, the uses of 2.8 N HCl was not preferred as the resulting extracts were difficult to concentrate and required excessive amounts of base to neutralize, resulting in a significant decrease in the concentration of the sapogenins and operational inefficiencies. For example, the use of acid strengths greater than 1 N may require glass reactors.

Figure 8:
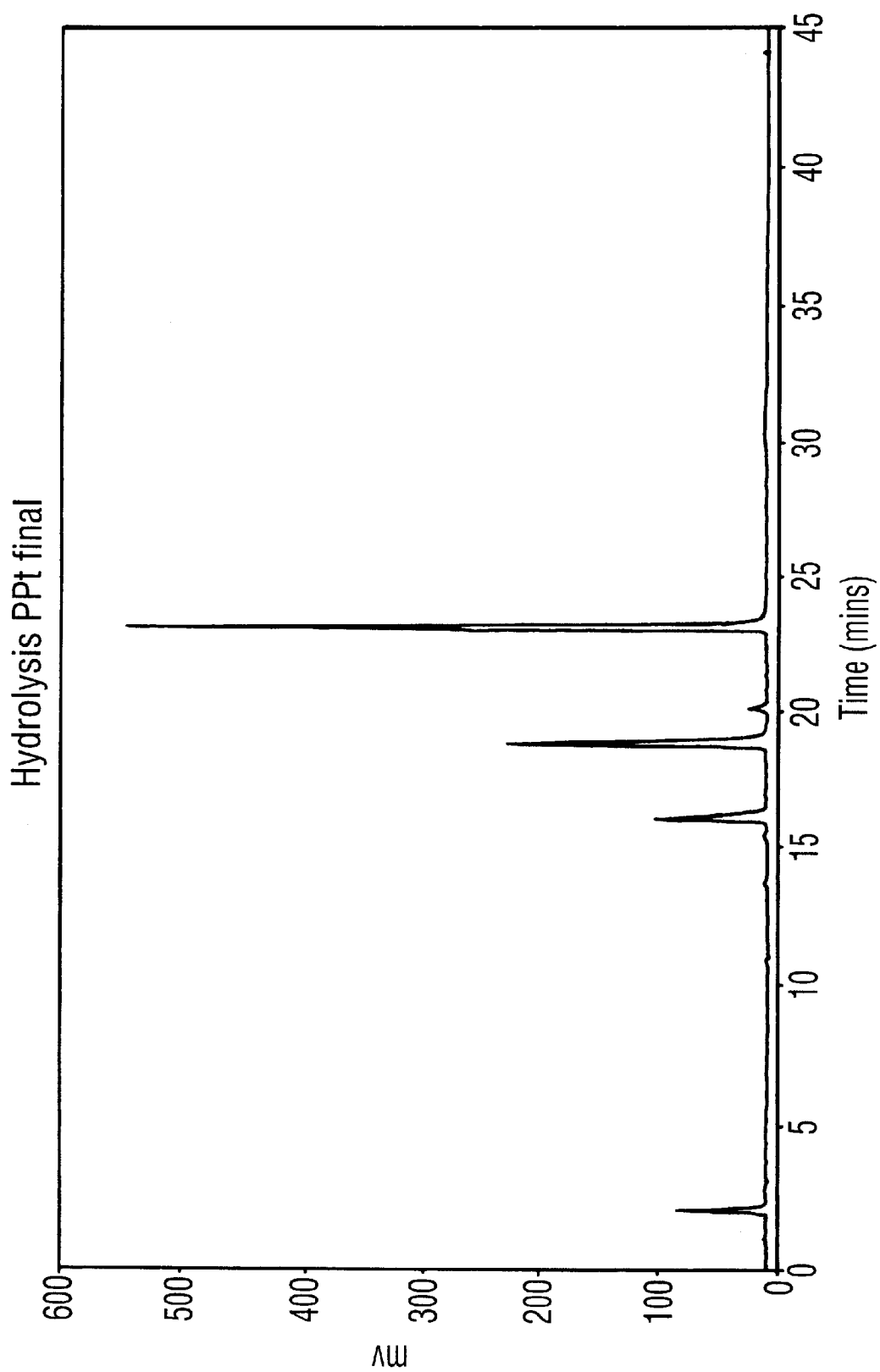
FIG. 8 depicts the RP-HPLC analysis of the mixture of sapogenins obtained after acid hydrolysis of the spray-dried aqueous ethanolic extract of quinoa bran. Waters Novapak C-18 (3.9×150 mm, 4 μm) eluted with a linear gradient of aqueous 0.05% TFA:acetonitrile containing 0.05% TFA (T=0,% $CH_3CN$=5; T=20,% $CH_3CN$=95) at a flow rate of 1 mL/min. The saponins were detected using ELSD.

For large scale production, milder conditions were found to be practical. The spray-dried extract (200 gm) was dissolved in 3 L of 50% ethanol and 450 mL of conc. HCl (pH 2) (1.58 N) and refluxed for 7 hours. The hydrolyzed extract is allowed to cool and the resulting dark brown precipitate is recovered by filtration (96.2 g). When the precipitate is slurried in water (2 L) and adjusted to pH 11 with 50% w/w NaOH, the pigmented material remains in solution leaving an off-white crystalline precipitate. The resulting crystalline precipitate was recovered by filtration, washed with dilute acid (1 L of 0.5 N HC1), followed by water (5 L) until the effluent is no longer coloured with a yield of 54.8 grams. The resulting product is an off-white powder that contains approximately 80% sapogenin comprising approximately equal amounts of the three sapogenins present (oleanolic acid, hederagenin and phytolaccagenic acid in a ratio of 2:4:4) (FIG. 8). The structure of the sapogenins was confirmed by standard analytical techniques including LC-MS, $^1$H-NMR and $^{13}$C-NMR.

Example 7

Purification of Sapogenins by Solid Phase Extraction

Figure 9A:
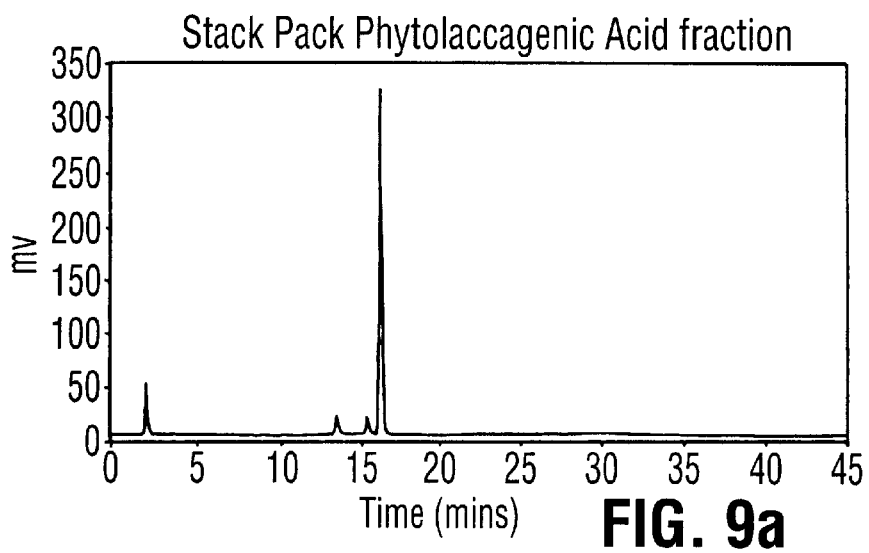
FIGS. 9A, 9B and 9C depict the RP-HPLC analysis of the sapogenin fractions obtained by SPE fractionation of the crude sapogenin mixture.
Figure 9B:
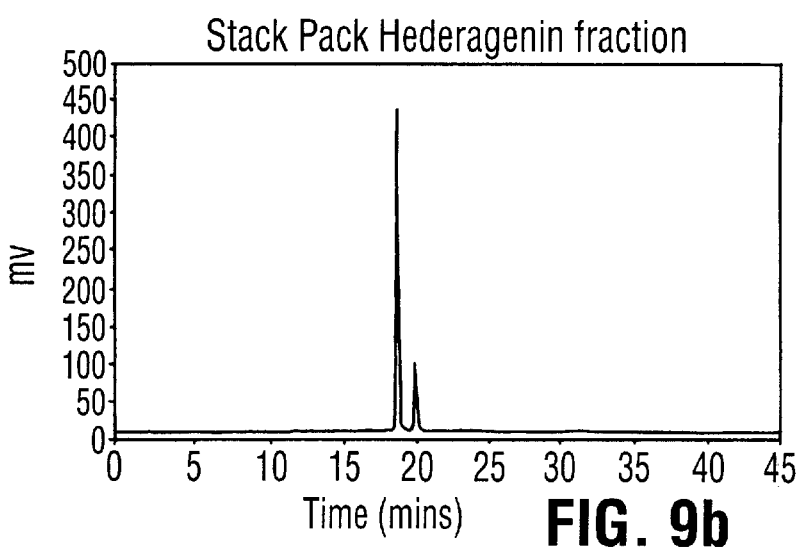
Figure 9C:
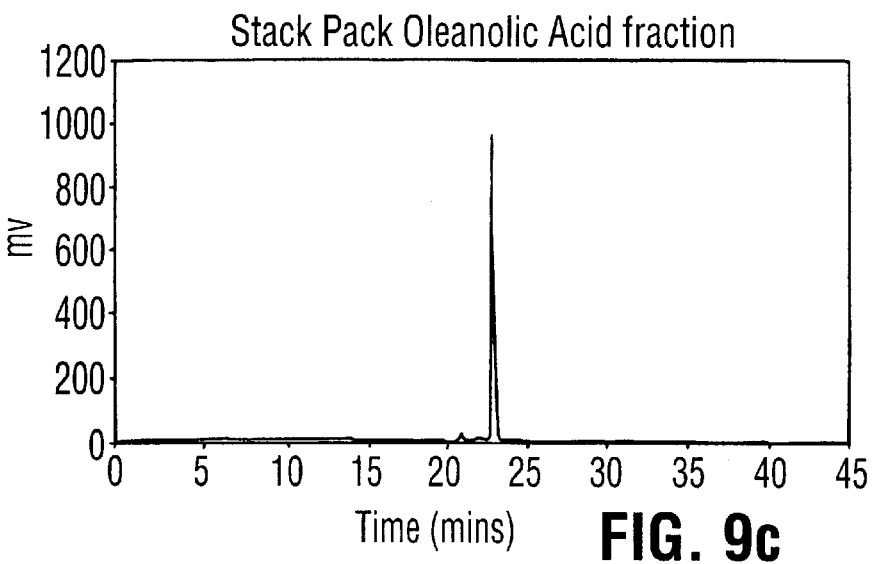

A crude sapogenin mixture (150 g) (FIG. 8) prepared by acid hydrolysis of the aqueous alcohol extract of quinoa bran is dissolved in 60% methanol adjusted to pH 9 with sodium hydroxide. The mildly basic solution is pumped onto a solid phase extraction (SPE) cartridge (17 L) and washed with 60% methanol (neutral pH). Further elution of the SPE cartridge with 60% methanol yields a fraction that is essentially pure phytolaccagenic acid (FIG. 9a). Sequential elution of the SPE cartridge with 70% and 85% methanol yields fractions that are essentially pure hederagenin (FIG. 9b), and pure oleanolic acid (FIG. 9c) respectively. The sapogenins thus obtained may be further purified by recrystallization from hot methanol or hot 95% alcohol, and/or preparative HPLC on RP-HPLC preparative columns eluted with Methanol and aqueous acetic acid to obtain the desired levels of purity.

What is claimed is:

1. A process for extraction of saponins from quinoa, comprising:

contacting a saponin-containing part of a quinoa plant with an aqueous alcohol solution containing about 55 to 75% v/v of an alcohol selected from the group consisting of methanol and ethanol to form a saponin-containing solution and an extracted solid residue, removing the alcohol from the saponin-containing solution to leave a saponin-containing aqueous solution, and evaporating water from the saponin-containing aqueous solution to produce a saponin-containing product.

2. The process of claim 1, wherein the aqueous alcohol solution contains 55 to 60% v/v alcohol by volume.

3. The process of claim 1, wherein the alcohol is methanol.

4. The process of claim 1, wherein the alcohol is ethanol.

5. The process of claim 1, wherein the aqueous alcohol solution has a boiling point, and the solution is contacted with the saponin-containing part of the quinoa plant at a temperature between ambient temperature and the boiling point of the solution.

6. The process of claim 1, wherein contact of the aqueous alcohol solution with the saponin-containing part of the quinoa plant is carried out at a ratio of aqueous alcohol solution to saponin-containing part of at least 8:1 v/w.

7. The process of claim 1, wherein contact of the aqueous alcohol solution with the saponin-containing part of the quinoa plant is carried out at a ratio of aqueous alcohol solution to saponin-containing part of at least 10:1 v/w.

8. The process of claim 1, wherein contact of the aqueous alcohol solution with the saponin-containing part of the quinoa plant is carried out at a ratio of aqueous alcohol solution to saponin-containing part in the range of 8:1 to 30:1 v/w.

9. The process of claim 1, wherein contact of the aqueous alcohol solution with the saponin-containing part of the quinoa plant is carried out at a liquid to solids ratio in the range of 10:1 to 15:1 v/w.

10. The process of claim 1, wherein the alcohol is removed from the saponin-containing solution by flash evaporation.

11. The process of claim 1, wherein the water is evaporated from the saponin-containing aqueous solution by spray drying.

12. The process of claim 1, wherein the saponin-containing solution is separated from the solid extracted residue before the alcohol is removed from the saponin-containing solution.

13. The process of claim 1, wherein the saponin-containing part of the quinoa plant is selected from the group consisting of whole seeds, ground seeds, seed coat, quinoa flour and quinoa bran.

14. The process of claim 1, wherein the saponin-containing part of the guinoa plant is quinoa bran.

15. The process of claim 1, wherein the saponin-containing product is subjected to purification to form a purified saponin-containing product.

16. The process of claim 15, wherein the purification is carried out by subjecting a solution containing the saponin-containing product to ultrafiltration.

17. The process of claim 16, wherein the ultrafiltration is carried out over an ultrafiltration membrane that has a molecular weight cut-off in the range between 200 and 3500.

18. The process of claim 17, wherein the membrane has a molecular weight cut-off in the range between 200 and 1000.

19. The process of claim 18, wherein the membrane has a molecular weight cut-off of about 1000.

20. The process of claim 15, wherein the purified saponin-containing product is separated into a plurality of different individual saponins.

21. The process of claim 20, wherein the individual saponins are separated by partitioning the purified saponin-containing product between immiscible aliphatic alcohol and aqueous solutions to form separate solutions of aliphatic alcohol-soluble saponins and water-soluble saponins, separately absorbing the saponins from the solutions on a solid phase, and sequentially eluting the solutions from the solid phase with aqueous alcohol to form individual saponin products.

22. The process of claim 21, wherein the solid phase is a C-8 or C-18 reverse-phase resin.

23. The process of claim 21, wherein the aliphatic alcohol is selected from the group consisting of n-butanol, 1-pentanol, 1-hexanol, 1-heptanol and 1-octanol.

24. The process of claim 21, wherein the aliphatic alcohol is n-butanol.

25. The process of claim 21, wherein the individual saponin products are further purified by recrystallization from methanol at a temperature of 50° C. or higher.

26. The process of claim 21, wherein the individual saponin products are further purified by preparative HPLC on RP-chromatography.

27. A process of purifying a mixture of saponins extracted from a saponin-containing part of a quinoa plant, comprising:

dissolving the mixture of saponins in a solvent to form a solution, and subjecting the solution to ultrafiltration over a membrane that has a molecular weight cut-off in the range of 200 to 300.

28. The process of claim 27, wherein the purified saponin-containing product is separated into a plurality of different individual saponins.

29. The process of claim 28, wherein the individual saponins are separated by partitioning the purified saponin-containing product between immiscible aliphatic alcohol and aqueous solutions to form separate solutions of aliphatic alcohol-soluble saponins and water-soluble saponins, and separately absorbing the saponins from the solutions on a solid phase, and sequentially eluting the solutions from the solid phase with aqueous alcohol to form individual saponin products.

30. The process of claim 29, wherein the solid phase is a C-8 or C-18 reverse-phase resin.

31. The process of claim 29, wherein the aliphatic alcohol is selected from the group consisting of n-butanol, 1-pentanol, 1-hexanol, 1-heptanol and 1-octanol.

32. The process of claim 29, wherein the aliphatic alcohol is n-butanol.

33. The process of claim 29, wherein the individual saponin products are further purified by recrystallization from methanol at a temperature of 50° C. or higher.

34. The process of claim 29, wherein the individual saponin products are further purified by preparative HPLC on RP-chromatography.

35. A process of producing sapogenins from corresponding saponins obtained by extraction from a quinoa plant, comprising:

obtaining a solution of saponins in an aqueous alcohol, adding an acid having a strength of 1–3.5 N to the solution to hydrolyze the saponins to form corresponding sapogenins that precipitates out of the solution as a precipitate, recovering the precipitate, and decolorizing the precipitate by forming a slurry of the precipitate with a solution of an aqueous base to form a decolorized sapogenin product.

36. The process of claim 35, which further comprises separating different individual sapogenins from the decolorized mixture.

37. The process of claim 36, wherein said different individual sapogenins are separated from the delcolorized sapogenin product by absorption of the product onto a solid phase and by carrying out sequential elution of the individual sapogenings from the solid phase by an aqueous alcohol.

38. The process of claim 37, wherein the individual sapogenins eluted from the solid phase are further purified by recrystallization from methanol at a temperature of 50° C. or higher.

39. The process of claim 37, wherein the solid phase is a C-8 or C-18 reverse-phase resin.

40. The process of claim 35, wherein the acid is selected from the group consisting of hydrochloric acid and sulphuric acid.

41. The process of claim 35, wherein the aqueous base is sodium hydroxide.

42. The process of claim 35, wherein the decolorized sapogenin product is washed with acid at a strength of less than 1 N prior to separation of the individual sapogenins.

43. The process of claim 35, wherein said acid is hydrochloric acid added at a strength of up to 3N.

44. The process of claim 35, wherein, following addition of said acid, the solution is heated under reflux.

45. The process of claim 44, wherein said heating under reflux is carried out for 2 to 8 hours.

46. The process of claim 35, wherein the saponins are obtained as a saponin-containing product from a quinoa plant by contacting a saponin-containing part of the quinoa plant with an aqueous alcohol solution containing an alcohol selected from the group consisting of methanol and ethanol to form a saponin-containing solution and an extracted solid residue, removing the alcohol from the saponin-containing solution to leave a saponin-containing aqueous solution, and evaporating water from the saponin-containing aqueous solution to produce the saponin-containing product.

47. A method of monitoring saponin and/or sapogenin contents of saponin-containing and/or sapogenin-containing products, comprising:

obtaining a saponin-containing and/or sapogenin-containing product as a solution in an aqueous alcohol solvent, performing HPLC analysis by RP-chromatography said product including elution with an organic acid in water-:methanol or water:acetonitrile to form eluted products, and detecting saponins or sapogenins in the eluted products by evaporative light scattering detection.

48. The method of claim 47, wherein the organic acid is selected from the group consisting of acetic acid and trifluoracetic acid.

49. A process for the extraction and purification of saponins from qunioa comprising extraction of quninoa comprising extraction of qunioa with mixing aqueous alcohols at a ratio of mixed aqueous alcohols to qunioa of at least 10:1 v/w at temperatures greater than ambient and less than the boiling point of the solvent, separation of liquids from solids, removal of alcohol, reduction of the extract to a saponin rich powder, concentration and fractionation of qunioa saponins comprising concentration and purification of saponins by ultrafiltration over a low molecular weight membrane, and fractionation into individual saponins by sequential elution from a solid phase extraction cartridge by aqueous alcohol.

50. A process for the conversion of quinoa saponins to produce their corresponding sapogenins comprising hydrolysis of the aqueous alcoholic extract of quinoa with a strong acid, recovery of the resulting precipitated sapogenins, decolorization of the concentrated crude sapogenin mixture by slurrying with aqueous base and fractionation into individual sapogenins by sequential elution from a solid phase extraction cartridge by aqueous alcohol.

\* \* \* \* \*